(12) United States Patent
Wong et al.

(10) Patent No.: US 10,688,283 B2
(45) Date of Patent: Jun. 23, 2020

(54) INTEGRATED CATHETER AND GUIDE WIRE CONTROLLER

(71) Applicant: Auris Health, Inc., Redwood City, CA (US)

(72) Inventors: Serena H. Wong, Mountain View, CA (US); Sean Paul Walker, Fremont, CA (US); June Park, San Jose, CA (US); Richard Henderson, Fremont, CA (US)

(73) Assignee: Auris Health, Inc., Redwood City, CA (US)

( * ) Notice: Subject to any disclaimer, the term of this patent is extended or adjusted under 35 U.S.C. 154(b) by 562 days.

(21) Appl. No.: 15/400,656

(22) Filed: Jan. 6, 2017

(65) Prior Publication Data

US 2017/0113019 A1    Apr. 27, 2017

Related U.S. Application Data

(63) Continuation of application No. 13/800,261, filed on Mar. 13, 2013, now Pat. No. 9,566,414.

(51) Int. Cl.
| | |
|---|---|
| *A61M 25/01* | (2006.01) |
| *A61B 34/30* | (2016.01) |
| *A61B 34/00* | (2016.01) |
| *A61M 25/09* | (2006.01) |

(52) U.S. Cl.
CPC ......... *A61M 25/0105* (2013.01); *A61B 34/30* (2016.02); *A61B 34/74* (2016.02); *A61M 25/09* (2013.01); *A61B 2034/301* (2016.02); *A61B 2034/742* (2016.02); *A61M 2205/502* (2013.01)

(58) Field of Classification Search
CPC combination set(s) only.
See application file for complete search history.

(56) References Cited

U.S. PATENT DOCUMENTS

| | | |
|---|---|---|
| 4,771,262 A | 9/1988 | Reuss |
| 4,896,554 A | 1/1990 | Culver |
| 5,008,528 A * | 4/1991 | Duchon ............... G06F 1/1632 |
| | | 250/221 |
| 5,176,310 A | 1/1993 | Akiyama et al. |
| 5,280,781 A | 1/1994 | Oku |
| 5,366,444 A | 11/1994 | Martin |

(Continued)

FOREIGN PATENT DOCUMENTS

| | | |
|---|---|---|
| CN | 102151134 | 8/2011 |
| CN | 202044721 U | 11/2011 |

(Continued)

*Primary Examiner* — Sean P Dougherty
(74) *Attorney, Agent, or Firm* — Knobbe, Martens, Olson & Bear LLP (57) ABSTRACT

A device may operate a guide wire and be operable by a single operator digit. The device may include an insertion control device for advancing the guide wire in a forward and in a reverse direction and along a longitudinal axis of the guide wire; and a rotary device for rolling a guide wire about the longitudinal axis. A robotic instrument driver may be operatively coupled to the device and configured to control axial movement of the guide wire along the longitudinal axis according to input received from the insertion control device and to control rotational movement of the guide wire according to input received from the rotary device.

30 Claims, 5 Drawing Sheets

(56) References Cited

U.S. PATENT DOCUMENTS

| | | |
|---|---|---|
| 5,398,691 A | 3/1995 | Martin et al. |
| 5,408,409 A | 4/1995 | Glassman et al. |
| 5,499,632 A | 3/1996 | Hill et al. |
| 5,524,180 A | 6/1996 | Wang et al. |
| 5,526,812 A | 6/1996 | Dumoulin et al. |
| 5,631,973 A | 5/1997 | Green |
| 5,713,946 A | 2/1998 | Ben-Haim |
| 5,749,362 A | 5/1998 | Funda et al. |
| 5,762,458 A | 6/1998 | Wang et al. |
| 5,831,614 A | 11/1998 | Tognazzini et al. |
| 5,859,934 A | 1/1999 | Green |
| 5,876,325 A | 3/1999 | Mizuno et al. |
| 5,899,851 A | 5/1999 | Koninckx |
| 5,951,475 A | 9/1999 | Gueziec et al. |
| 5,963,770 A | 10/1999 | Eakin |
| 6,007,550 A | 12/1999 | Wang et al. |
| 6,016,439 A | 1/2000 | Acker |
| 6,038,467 A | 3/2000 | De Bliek et al. |
| 6,096,004 A | 8/2000 | Meglan et al. |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,425,865 B1 | 7/2002 | Salcudean et al. |
| 6,466,198 B1 | 10/2002 | Feinstein |
| 6,468,265 B1 | 10/2002 | Evans et al. |
| 6,516,421 B1 | 2/2003 | Peters |
| 6,551,281 B1 | 4/2003 | Raulerson et al. |
| 6,690,964 B2 | 2/2004 | Beiger et al. |
| 6,726,675 B1 | 4/2004 | Beyar |
| 6,856,827 B2 | 2/2005 | Seeley et al. |
| 7,155,315 B2 | 12/2006 | Niemeyer et al. |
| 7,594,925 B2 | 9/2009 | Danek |
| 8,180,114 B2 | 5/2012 | Nishihara et al. |
| 8,718,837 B2 | 5/2014 | Wang et al. |
| 8,971,597 B2 | 3/2015 | Zhao et al. |
| 9,014,851 B2 | 4/2015 | Wong et al. |
| 9,057,600 B2 | 6/2015 | Walker et al. |
| 9,138,166 B2 | 9/2015 | Wong et al. |
| 9,241,767 B2 * | 1/2016 | Prisco .................... B25J 9/1674 |
| 9,271,663 B2 | 3/2016 | Walker et al. |
| 9,283,046 B2 | 3/2016 | Walker et al. |
| 9,289,578 B2 | 3/2016 | Walker et al. |
| 9,498,291 B2 | 11/2016 | Balaji et al. |
| 9,503,681 B1 | 11/2016 | Popescu et al. |
| 9,504,604 B2 | 11/2016 | Alvarez |
| 9,532,840 B2 | 1/2017 | Wong et al. |
| 9,561,019 B2 | 2/2017 | Mihailescu et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,770,216 B2 | 9/2017 | Brown et al. |
| 9,788,910 B2 | 10/2017 | Schuh |
| 9,818,681 B2 | 11/2017 | Machida |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,223 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,123,755 B2 | 11/2018 | Walker et al. |
| 10,130,427 B2 | 11/2018 | Tanner et al. |
| 10,145,747 B1 | 12/2018 | Lin et al. |
| 10,159,532 B1 | 12/2018 | Ummalaneni et al. |
| 10,285,574 B2 | 5/2019 | Landey et al. |
| 10,346,976 B2 | 7/2019 | Averbuch |
| 2002/0077533 A1 | 6/2002 | Bieger et al. |
| 2002/0120188 A1 | 8/2002 | Brock et al. |
| 2002/0161280 A1 | 10/2002 | Chatenever et al. |
| 2004/0047044 A1 | 3/2004 | Dalton |
| 2004/0263535 A1 | 12/2004 | Birkenbach et al. |
| 2005/0085714 A1 | 4/2005 | Foley et al. |
| 2005/0193451 A1 | 9/2005 | Quistgaard et al. |
| 2006/0025676 A1 | 2/2006 | Viswanathan et al. |
| 2006/0079745 A1 | 4/2006 | Viswanathan et al. |
| 2006/0095022 A1 | 5/2006 | Moll et al. |
| 2006/0173290 A1 | 8/2006 | Lavallee et al. |
| 2006/0190034 A1 | 8/2006 | Nishizawa et al. |
| 2007/0083098 A1 | 4/2007 | Stern et al. |
| 2007/0138992 A1 | 6/2007 | Prisco et al. |
| 2007/0144298 A1 | 6/2007 | Miller |
| 2007/0185486 A1 | 8/2007 | Hauck et al. |
| 2008/0027313 A1 | 1/2008 | Shachar |
| 2008/0082109 A1 * | 4/2008 | Moll ..................... A61B 34/30 606/130 |
| 2008/0097465 A1 | 4/2008 | Rollins et al. |
| 2008/0108870 A1 | 5/2008 | Wiita et al. |
| 2008/0140087 A1 | 6/2008 | Barbagli et al. |
| 2008/0159653 A1 | 7/2008 | Dunki-Jacobs et al. |
| 2008/0183068 A1 | 7/2008 | Carls et al. |
| 2008/0183188 A1 | 7/2008 | Carls et al. |
| 2008/0306490 A1 | 12/2008 | Lakin et al. |
| 2009/0248036 A1 | 10/2009 | Hoffman et al. |
| 2009/0259230 A1 | 10/2009 | Khadem |
| 2009/0259412 A1 | 10/2009 | Brogardh |
| 2009/0326322 A1 * | 12/2009 | Diolaiti ............. A61B 1/00039 600/112 |
| 2009/0326556 A1 | 12/2009 | Diolaiti et al. |
| 2010/0019890 A1 | 1/2010 | Helmer et al. |
| 2010/0039506 A1 | 2/2010 | Sarvestani et al. |
| 2010/0057045 A1 | 3/2010 | Albritton et al. |
| 2010/0076263 A1 | 3/2010 | Tanaka |
| 2010/0121269 A1 | 5/2010 | Goldenberg |
| 2010/0125284 A1 | 5/2010 | Tanner et al. |
| 2010/0161129 A1 | 6/2010 | Costa et al. |
| 2010/0204613 A1 | 8/2010 | Rollins et al. |
| 2010/0225209 A1 | 9/2010 | Goldberg |
| 2010/0328455 A1 | 12/2010 | Nam et al. |
| 2011/0021926 A1 | 1/2011 | Spencer |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0196199 A1 | 8/2011 | Donhowe et al. |
| 2011/0235855 A1 | 9/2011 | Smith |
| 2011/0238010 A1 | 9/2011 | Kirschenman et al. |
| 2011/0248987 A1 | 10/2011 | Mitchell |
| 2011/0276058 A1 | 11/2011 | Choi et al. |
| 2011/0306873 A1 | 12/2011 | Shenai et al. |
| 2012/0059392 A1 | 3/2012 | Diolaiti |
| 2012/0071752 A1 | 3/2012 | Sewell |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0158011 A1 | 6/2012 | Sandhu |
| 2012/0203067 A1 | 8/2012 | Higgins et al. |
| 2012/0253276 A1 | 10/2012 | Govari et al. |
| 2012/0296161 A1 | 11/2012 | Wallace et al. |
| 2012/0314022 A1 | 12/2012 | Jo |
| 2013/0018306 A1 | 1/2013 | Ludwin |
| 2013/0060146 A1 | 3/2013 | Yang et al. |
| 2013/0165854 A1 | 6/2013 | Sandhu et al. |
| 2013/0317519 A1 | 11/2013 | Romo et al. |
| 2014/0111457 A1 | 4/2014 | Briden et al. |

(56) References Cited

U.S. PATENT DOCUMENTS

| | | |
|---|---|---|
| 2014/0142591 A1 | 5/2014 | Alvarez et al. |
| 2014/0222204 A1 | 8/2014 | Kawashima |
| 2014/0257334 A1 | 9/2014 | Wong et al. |
| 2014/0264081 A1 | 9/2014 | Walker et al. |
| 2014/0275985 A1 | 9/2014 | Walker et al. |
| 2014/0275988 A1 | 9/2014 | Walker et al. |
| 2014/0276392 A1 | 9/2014 | Wong et al. |
| 2014/0276394 A1 | 9/2014 | Wong et al. |
| 2014/0276646 A1 | 9/2014 | Wong et al. |
| 2014/0276934 A1 | 9/2014 | Balaji et al. |
| 2014/0276937 A1 | 9/2014 | Wong et al. |
| 2014/0276938 A1 | 9/2014 | Hsu et al. |
| 2014/0277333 A1 | 9/2014 | Lewis et al. |
| 2014/0277747 A1 | 9/2014 | Walker et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0018622 A1 | 1/2015 | Tesar et al. |
| 2015/0051592 A1 | 2/2015 | Kintz |
| 2015/0101442 A1 | 4/2015 | Romo |
| 2015/0105747 A1 | 4/2015 | Rollins et al. |
| 2015/0119638 A1 | 4/2015 | Yu et al. |
| 2015/0142013 A1 | 5/2015 | Tanner et al. |
| 2015/0157191 A1 | 6/2015 | Phee et al. |
| 2015/0164594 A1 | 6/2015 | Romo et al. |
| 2015/0164596 A1 | 6/2015 | Romo |
| 2015/0223902 A1 | 8/2015 | Walker et al. |
| 2015/0224845 A1 | 8/2015 | Anderson et al. |
| 2015/0265807 A1 | 9/2015 | Park et al. |
| 2015/0290454 A1 | 10/2015 | Tyler et al. |
| 2015/0297864 A1 | 10/2015 | Kokish et al. |
| 2015/0314110 A1 | 11/2015 | Park |
| 2015/0335480 A1 | 11/2015 | Alvarez et al. |
| 2015/0375399 A1 | 12/2015 | Chiu et al. |
| 2016/0001038 A1 | 1/2016 | Romo et al. |
| 2016/0007881 A1 | 1/2016 | Wong et al. |
| 2016/0026253 A1 | 1/2016 | Bradski et al. |
| 2016/0059412 A1 | 3/2016 | Oleynik |
| 2016/0098095 A1 | 4/2016 | Gonzalez-Banos et al. |
| 2016/0175059 A1 | 6/2016 | Walker et al. |
| 2016/0183841 A1 | 6/2016 | Duindam et al. |
| 2016/0202053 A1 | 7/2016 | Walker et al. |
| 2016/0213436 A1 | 7/2016 | Inoue |
| 2016/0213884 A1 | 7/2016 | Park |
| 2016/0228032 A1 | 8/2016 | Walker et al. |
| 2016/0270665 A1 | 9/2016 | Landey et al. |
| 2016/0287279 A1 | 10/2016 | Bovay et al. |
| 2016/0296294 A1 | 10/2016 | Moll et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0065356 A1 | 3/2017 | Balaji et al. |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0119413 A1 | 5/2017 | Romo |
| 2017/0119481 A1 | 5/2017 | Romo et al. |
| 2017/0143429 A1 | 5/2017 | Richmond et al. |
| 2017/0151027 A1 | 6/2017 | Walker et al. |
| 2017/0165011 A1 | 6/2017 | Bovay et al. |
| 2017/0172664 A1 | 6/2017 | Weingarten et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0056044 A1 | 3/2018 | Choi et al. |
| 2018/0078321 A1 | 3/2018 | Liao |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0090969 A1 | 3/2019 | Jarc et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0151032 A1 | 5/2019 | Mustufa et al. |
| 2019/0167361 A1 | 6/2019 | Walker et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |

FOREIGN PATENT DOCUMENTS

| | | |
|---|---|---|
| EP | 1 800 593 | 6/2007 |
| EP | 2 158 834 | 3/2010 |
| JP | 07-225343 | 8/1995 |
| WO | WO 03/086190 | 10/2003 |
| WO | WO 08/049088 | 4/2008 |
| WO | WO 10/025522 | 3/2010 |

* cited by examiner

INTEGRATED CATHETER AND GUIDE WIRE CONTROLLER

CROSS-REFERENCE TO RELATED APPLICATION

This application is a continuation of U.S. patent application Ser. No. 13/800,261, filed Mar. 13, 2013 and entitled "INTEGRATED CATHETER AND GUIDE WIRE CONTROLLER." The entirety of which is hereby incorporated by reference for all purposes.

BACKGROUND

Minimally invasive surgery (MIS) systems may utilize flexible robotic catheters that are navigated in the bloodstream of a patient and visualized using X-rays. MIS apparatus and techniques have advanced to the point where an elongated catheter instrument is controllable by selectively operating tensioning control elements within the catheter instrument. In one example, four opposing directional control elements wend their way to the distal end of the catheter which, when selectively placed in and out of tension, cause the distal end to steerably maneuver within the patient. Control motors are coupled to each of the directional control elements so that they may be individually controlled and the steering effectuated via the operation of the motors in unison.

A controller device includes an assortment of controls to allow an operator to maneuver the catheter instrument as well as a guide wire guided by the catheter instrument. Some controller devices employ buttons dedicated to control the catheter instrument and a second set of buttons to control the guide wire. Other controller devices include a joystick type controller to control the catheter, often one-handed, and a separate set of button controls to control the guide wire. For instance, gross hand motion of a joystick may be used to control the catheter, leaving the operator to use one's thumb and fine finger control to manipulate the guide wire. When controlling such catheter devices, coordinated motion of the catheter device and guide wire may be difficult to perform. Thus, such systems may lack the precision desired by operators of the robotic catheter system for performing MIS operations.

SUMMARY

An exemplary device for operating a guide wire may include an insertion control device for advancing the guide wire in a forward and reverse direction along a longitudinal axis of the guide wire; and a rotary device for rolling a guide wire about the longitudinal axis; wherein the device is operable by a single operator digit, allowing the rest of the operator hand to control a catheter.

An exemplary system may include a guide wire control device operable by a single operator digit and including an insertion control device for advancing a guide wire in a forward and reverse direction along a longitudinal axis of the guide wire, and a rotary device for rolling a guide wire about the longitudinal axis. The system may further include a robotic instrument driver operatively coupled to the guide wire control device and configured to control axial movement of the guide wire along the longitudinal axis according to input received from the insertion control device and to control rotational movement of the guide wire according to input received from the rotary device.

DETAILED DESCRIPTION

Figure 1:
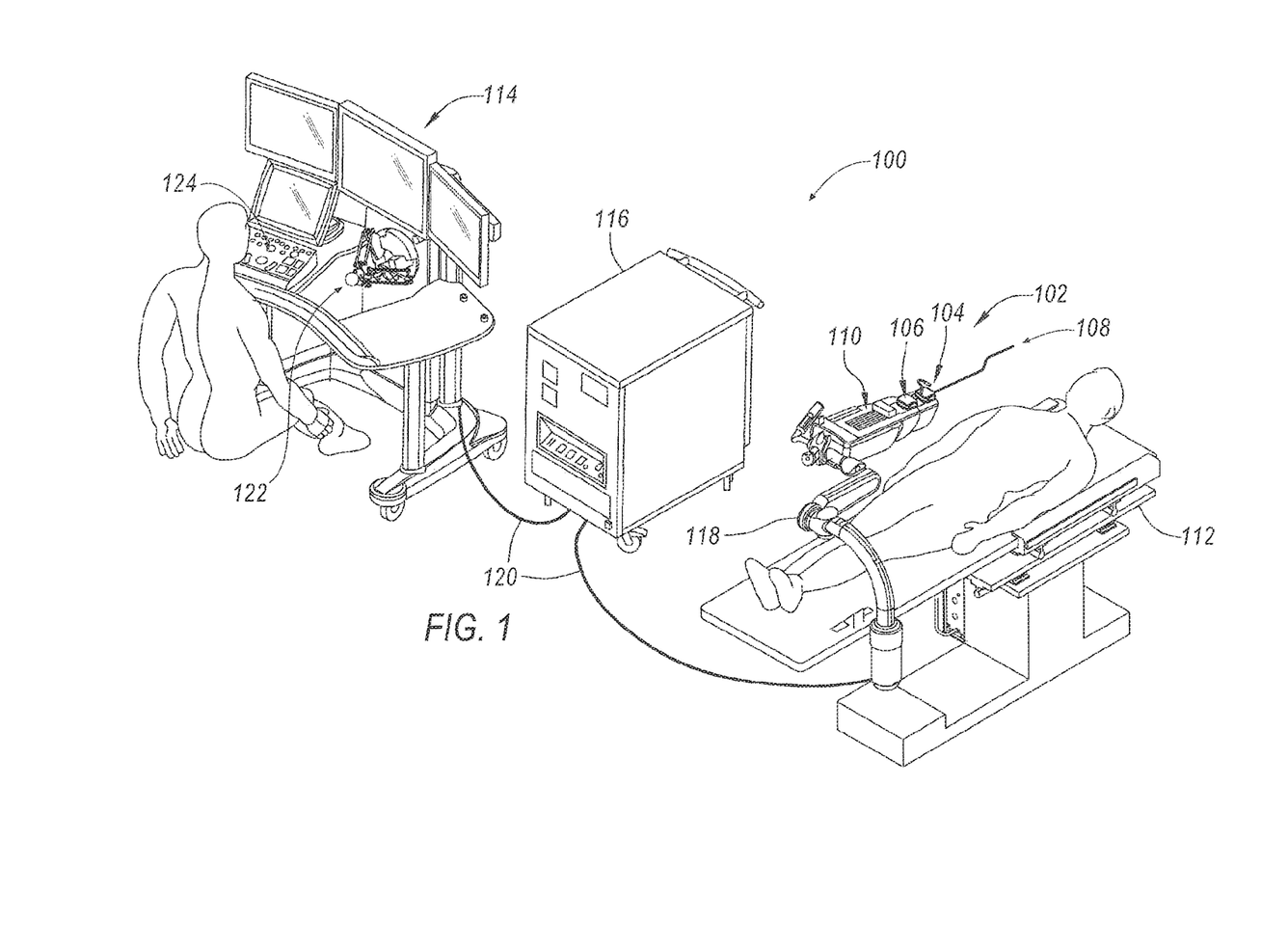
FIG. 1 illustrates an exemplary robotically controlled surgical system.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter 106" or "catheter instrument 106"). The catheter instrument 106 may further include a guide wire 108 extendable beyond a distal end of the catheter instrument 106. Catheter assembly 102 is controllable using a robotic instrument driver 110 (generally referred to as "instrument driver"). During use, a patient is positioned on an operating table or surgical bed 112 (generally referred to as "operating table") to which robotic instrument driver 110 is coupled or mounted. In the illustrated example, system 100 includes an operator workstation 114, an electronics rack 116 and associated bedside electronics box (not shown), a setup joint mounting brace 118, and instrument driver 110. A surgeon is seated at operator workstation 114 and can monitor the surgical procedure, patient vitals, and control one or more catheter devices.

System components may be coupled together via a plurality of cables or other suitable connectors 120 to provide for data communication, or one or more components may be equipped with wireless communication components to reduce or eliminate cables 120. Communication between components may also be implemented over a network or over the Internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

The operator workstation 114 may include a computer monitor configured to display a three dimensional object, such as a representation of the catheter instrument 106 and guide wire 108. The catheter instrument 106 and guide wire 108 may be displayed within or relative to a three dimensional space, such as a body cavity or organ, e.g., a chamber of a patient's heart.

The operator workstation 114 may further provide for control of the catheter 106 and guide wire 108. As one example, the operator workstation 114 may include a set of controls having a joystick type controller 122 and a keyboard type input device 124. The catheter 106 may be controlled using the joystick type controller 122 allowing for steering of the distal tip of the guide catheter 106 as viewed on the computer monitor display, while the guide wire 108 may be controlled using the keyboard type input device 124.

The joystick type controller 122 may further include various sensors to detect the position of the joystick type controller 122 and to provide signals to the controller that are interpreted as commands. The joystick type controller 122 may also include a control member configured to move about a pivot point along one or more axes. In some cases, additional controls such as buttons may be positioned on the control member or a base of the joystick type controller 122.

A variation of the keyboard type input device 124 of FIG. 1 may include controls for the sheath catheter and elongate member manipulator. The keyboard type input device 124 may include bend, insert and rotate controls to steer the sheath catheter, as well as rotate and insert controls to control the elongate member manipulator. In alternative variations, the distal tip of the guide wire 108 may be controlled using the joystick type controller 122 while the guide and sheath catheters may be controlled by the keyboard type input device 124.

However, controlling coordinated motion of the catheter 106 and guide wire 108 using the joystick type controller 122 in combination with the keyboard type input device 124 may be difficult for operators to perform. For example, to perform a spiraling motion for breaking friction in wire control, the operator may be required to perform precise actions with the joystick type controller 122 in one hand, and the keyboard type input device 124 in the other hand.

A device may be designed that allows for simultaneous guide wire 108 roll and guide wire 108 insertion operated by a single digit of the operator, allowing the rest of the operator hand to control a catheter 106. The digit may include the thumb or any of the four fingers of a hand. The device may be placed on a control member of the catheter control joystick 122, and may be utilized to provide for both rotational control of the guide wire 108 according to a rotary device and also axial control of the guide wire 108 device (e.g., insert, retract) by way of a separate but readily reachable insertion/retraction control aspect of the device. Various thumb and fine-finger devices such as rotational wheels and trackballs may be utilized as the rotary device in combination with guide wire 108 insertion control to provide for advanced command control features such as simultaneous roll and insertion of a guide wire 108, without requiring the operator to work with a second set of guide wire 108 or other controls.

Figures 2A, 2D:
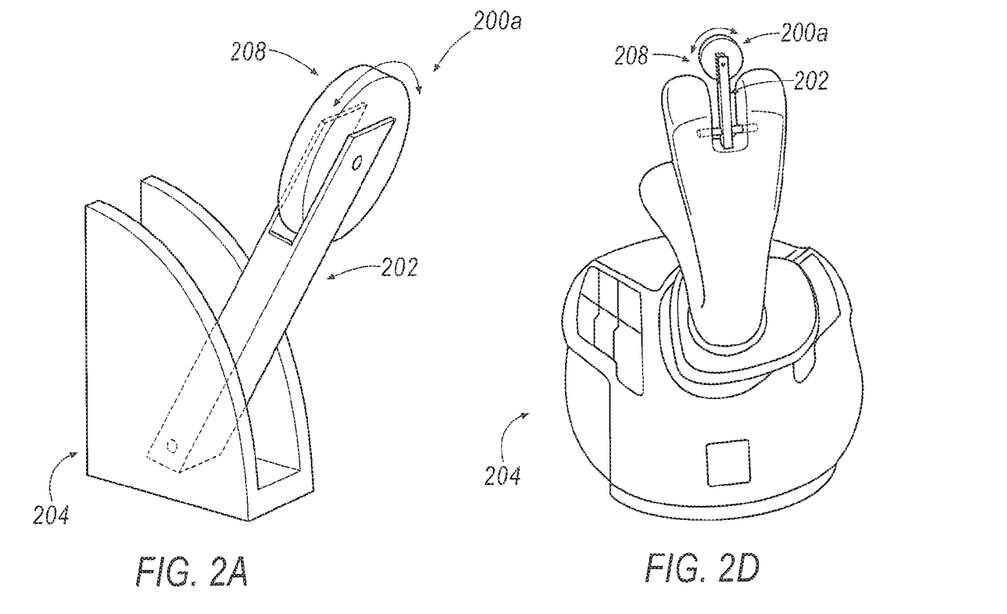
FIG. 2A illustrates an exemplary device having a pivotable insertion control member onto which a vertical rotary control is mounted.
FIG. 2D illustrates an exemplary device mounted to a control member of a joystick.

FIG. 2A illustrates an exemplary device 200-A having a pivotable insertion control member 202 onto which a vertical rotary control 208 is mounted. By providing for guide wire 108 insertion control using the insertion control member 202 and also guide wire 108 roll control using the vertical rotary control 208, the device 200 may facilitate single-digit performance of a spiraling insertion motion for breaking friction during wire control.

More specifically, a first end of the insertion control member 202 may be connected to a base member 204, such as by way of a pivot pin, bolt or hinge, thereby providing for forward and back pivoting motion of the insertion control member 202 about an axis of rotation. Tilt of the insertion control member 202 may be measured by way of a potentiometer or Hall Effect sensors mounted to turn along the pivot point, or switches mounted to the base member 204 that are selectively engaged and disengaged due to the pivoting movement of the insertion control member 202. Forward motion of the insertion control member 202 about the axis of rotation may be detected by the sensors, and provide for insertion control of a guide wire 108, while backward motion of the insertion control member 202 about the axis of rotation may also be detected by the sensors and may provide for retraction control (or a reverse control configuration). In some examples, a spring return or other biasing mechanism may further be included to center the insertion control member 202 to a midpoint or other intermediate point along its axis of rotation.

Since the pivot range of the insertion control member 202 may be relatively limited as compared to the insertion range of the guide wire 108, control of insert and retract may be performed according to velocity control, wherein the insertion control member 202 controls the velocity of the guide wire 108 insertion and retraction as opposed to direction or speed. Velocity may be calculated, for example, by comparing a current position of the insertion control member 202 in a current measurement cycle to the position of the insertion control member 202 in a previous measurement cycle. A maximum velocity limit may be used to cap the determined velocity to be within a predefined velocity limit. The predefined velocity limit may be related to factors such as a maximum speed of insertion or retraction capable of being performed by the system 100 or a safety threshold to protect the patient from high-velocity guide wire 108 movements.

The vertical rotary control 208 may be mounted vertically at a second end of the insertion control member 202, such that the vertical rotary control 208 may be free to rotate perpendicular to the axis of rotation of the insertion control member 202. The vertical rotary control 208 may be configured to measure an operator-applied rotation, such as by use of an infinite roll encoder, potentiometer or other rotational sensor, as some examples, and to apply the provided rotation to the guide wire 108. The vertical rotary control 208 may provide for an absolute position control mode (e.g., wherein a controlled drive mechanism follows the movements of the vertical rotary control 208), or a relative position control mode (e.g., in which rotation of the vertical rotary control 208 provides for a corresponding amount of roll of the guide wire 108 when the vertical rotary control 208 is in an active or clutched state but not when in an inactive or released clutch state).

For the roll component of the control, relative or absolute position control may be applicable modes of control because the guide wire 108 may experience whip, and in order to understand that whip is happening, an operator of the user interface device 200 may need to connect visual feedback with respect to actual wire roll (e.g., by using fluoroscope imaging displayed on the computer monitor display of the of the operator workstation 114) with an expected amount that the operator is turning the vertical rotary control 208. For instance, if the operator of the user interface device 200 has turned the vertical rotary control 208 by a full turn and the operator does not see movement in the guide wire 108 tip, the operator may infer that wind-up is occurring and that further rolling of the guide wire 108 should be avoided.

Figures 2B, 2C:
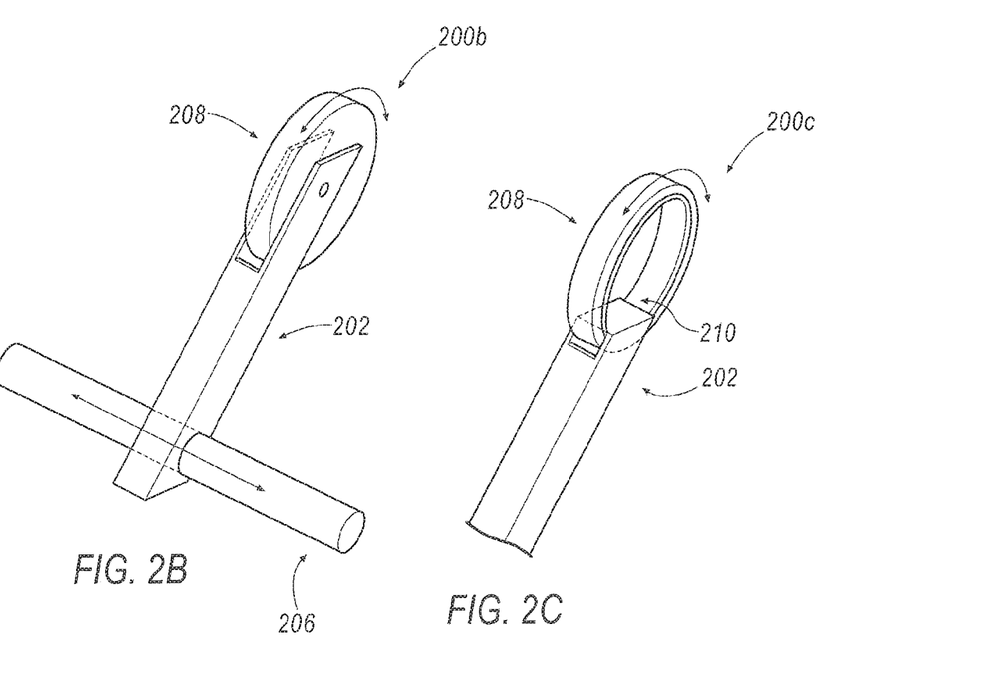
FIG. 2B illustrates an exemplary device having a slidable insertion control member onto which a vertical rotary control is mounted.
FIG. 2C illustrates an exemplary rotary control having a digit rest suitable for use with the exemplary devices of FIGS. 2A and 2B.

FIG. 2B illustrates an alternate exemplary device 200-B having a slidable insertion control member 202 onto which the vertical rotary control 208 is mounted. Thus, rather than providing bi-directional guide wire 108 insertion control by pivoting about a point as done in the exemplary device 200-A, in the exemplary device 200-B the insertion control member 202 may be positioned on a slider that slides backwards and forwards in a linear motion along an axis.

Exemplary slider implementations may include tongue-in-groove attachments or other suitable couplings facilitating movement of the insertion control member 202 along an articulation path 206. The path 206 may be supported in various ways, such as by one or more end supports holding the path 206 in place to a base member 204. Location of the insertion control member 202 along the slide may be measured in various ways, such as according to a connection of the insertion control member 202 to a linear potentiometer or other sensor attached to the slide, as one example. Forward motion of the insertion control member 202 along the articulation path 206 may therefore provide for sensed insertion control of a guide wire 108, while backward motion of the insertion control member 202 along the articulation path 206 may provide for sensed retraction control (or a reverse control configuration). As with the pivotable insertion control member 202 of device 200-A, the slidable insertion control member 202 of device 200-B may include a biasing mechanism to center the insertion control member 202 to a midpoint or other point along its slidable axis.

The slidable insertion control member 202 may operate in a variety of control modes, such as in a position control mode or in a velocity control mode. As a further example, the slidable insertion control member 202 may operate in a combination control mode in which the position control mode may be utilized in the center range of the articulation path 206 of the slider and the velocity control mode may be utilized near the ends of the articulation path 206 range.

FIG. 2C illustrates an alternate exemplary vertical rotary control 208 having a digit rest 210 suitable for use with the exemplary devices of FIGS. 2A and 2B. The exemplary vertical rotary control 208 may include a digit rest 210 formed by way of a hollow ring or other opening, such that a thumb or other digit of a hand of an operator may pass through. An outer ring vertical rotary control 208 may surround the digit rest 210 and may measure an operator-applied rotation, such as by use of an infinite roll encoder, potentiometer or other rotational sensor, as some examples. Another digit of the hand, such as an index finger, may engage the outside surface of the outer ring vertical rotary control 208, such that the operator may apply the rotational motion to the ring vertical rotary control 208. The alternate exemplary vertical rotary control 208 may accordingly provide for full rotation of the wheel by the operator, while still allowing for insert and retraction control by way of the pivotable or slideable insertion control members 202 described in detail above.

FIG. 2D illustrates an exemplary device 200-A mounted to a control member of a joystick 122. As illustrated, the device 200-A may be utilized to provide for both rotational control of the guide wire 108 according to the rotary device 208 and also axial control of the guide wire 108 device (e.g., insert, retract) by movement of the control member 202. Control of the catheter may also be performed according to the catheter control functions of the joystick device 122. While the device 200-A is illustrated, it should be noted that other guide wire 108 control devices, including any of the exemplary devices 200 or 300 discussed herein, may similarly be mounted to the joystick 122 control member.

Figure 3A:
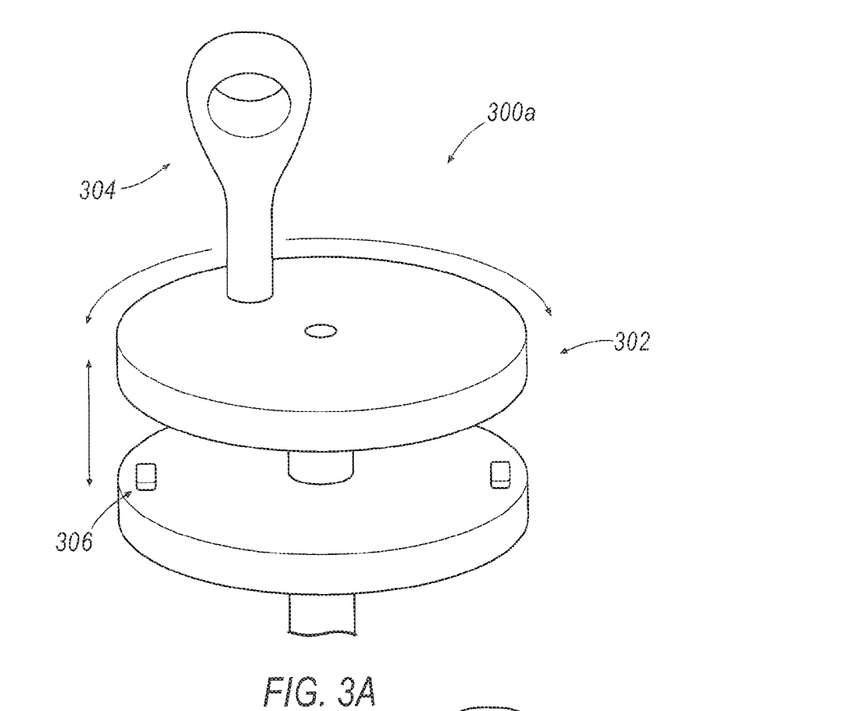
FIG. 3A illustrates an exemplary device including a horizontal rotary control and a digit rest.

FIG. 3A illustrates an exemplary device 300-A including a horizontal rotary control 302 and digit holder 304. As with the device 200, the device 300 may also provide for rotational control of the guide wire 108 as well as bidirectional insertion control of the guide wire 108, performed according to a separate motion of the device 300 in combination with the rotary control.

In the exemplary device 300-A, an axle or other support may be fixed to a base member at a first end, and to a horizontal rotary control 302 at the second end. The horizontal rotary control 302 may include a wheel attached to the support at or near the second end of the base member, such that the wheel may be free to rotate about the support on an axis of rotation extending along the axis of the support. The support may further include a groove or other slide path allowing the wheel to translate a distance along axis of rotation. The horizontal rotary control 302 may further include a second wheel or other surface onto which one or more switches 306 or other sensors 306 facing the first wheel may be mounted. The sensors 306 may be capable of detecting translation movement of the wheel along the axis of rotation, such as according to switches having selective mechanical engagement with the first wheel, or a type of proximity sensor 306 such as an infrared, capacitive, or inductive sensor 306. In some examples, translation of the first wheel toward the sensors 306 may provide for insertion control, while translation of the first wheel in an opposite direction away from the switches may provide for retraction control.

A first end of a thumb holder axle or other support member may be affixed to the top face of the first wheel, on the side opposite the wheel support, and at a location offset from the center of the first wheel. The digit holder 304 may be connected to the digit holder support such that the digit holder 304 may freely rotate about the axis of the support. The digit holder 304 may be formed by way of a hollow ring or other opening such that a digit may pass into and rest within the enclosed space. An operator may insert a digit into the digit holder 304 and may use the digit holder 304 to rotationally drive the first wheel of the horizontal rotary control 302 such that the digit may remain in substantially the same orientation throughout the rotation. Moreover, due to the digit holder 304 encircling the operator digit, the operator may push or pull the digit holder 304 along the axis of rotation, thereby pushing or pulling the horizontal rotary control 302, in turn causing the sensors 306 to detect the translation and provide for guide wire 108 insertion control. The horizontal rotary control 302 may further include a biasing mechanism to center the first wheel to a midpoint along its slidable axis.

Figure 3B:
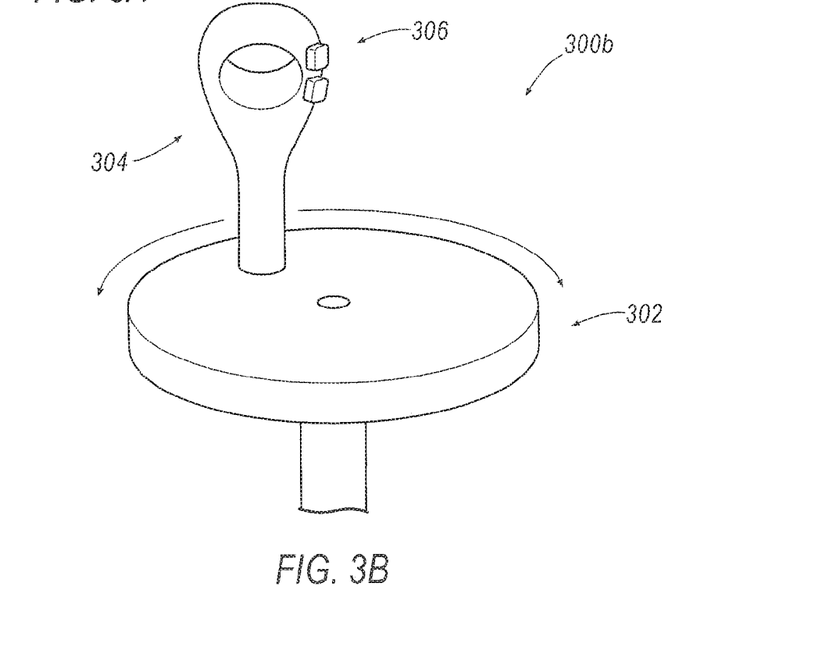
FIG. 3B illustrates an alternate exemplary device including a horizontal rotary control and a digit rest including insert and retract buttons.

FIG. 3B illustrates an alternate exemplary device 300-B including a horizontal rotary control 302 and a digit holder 304 including insert and retract buttons. As with the device 300-A, the device 300-B may provide for rotational control of the guide wire 108 according to a horizontal rotary control 302 having a digit holder 304. However, instead of providing bidirectional insertion control of the guide wire 108 according to translation of the horizontal rotary control 302, the device 300-B instead includes guide wire controls 306 (e.g., an insert button and a retract button) mounted on an exterior surface of the digit holder 304. Accordingly, an operator may insert a digit into the digit holder 304 to rotationally drive the horizontal rotary control 302, and may use another digit to press the insert button and retract buttons to provide for guide wire 108 insertion control. For instance, the operator may insert a thumb into the digit holder 304, and may utilize the insert button and retract buttons using an index finger in a pinching motion.

Figure 3C:
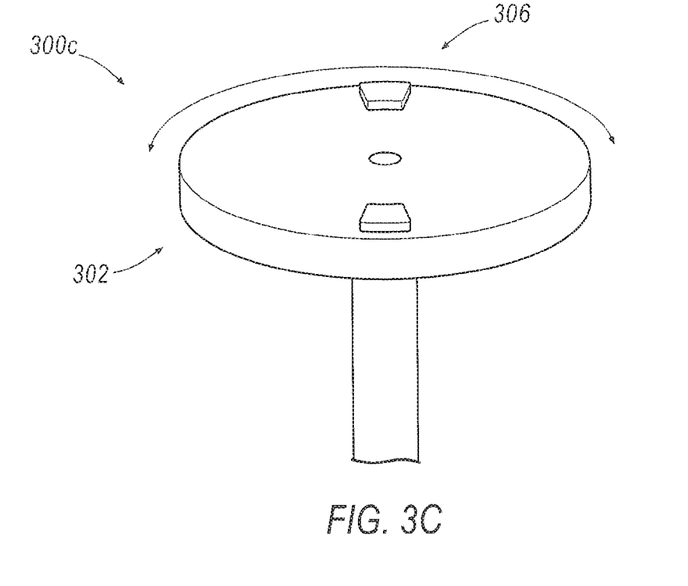
FIG. 3C illustrates an alternate exemplary device including a horizontal rotary control and insert and retract buttons.

FIG. 3C illustrates an alternate exemplary device 300-C including a horizontal rotary control 302 and insert and retract buttons. As with the devices 300-A and 300-B, the device 300-B may provide for rotational control of the guide wire 108 according to a horizontal rotary control 302. To provide for guide wire 108 insertion control, guide wire controls 306 such as an insert button and a retract button may be mounted on the horizontal rotary control 302 on the top surface opposite the support. To facilitate use of the insert button and a retract button for guide wire 108 insertion control, the buttons may be visibly marked as being assigned to the insert or retract functions. Moreover, to allow for control of guide wire 108 insertion while looking elsewhere than the face of the horizontal rotary control 302 (e.g., viewing an insertion site, viewing a fluoroscope or computer monitor display of the operator workstation 114, etc.), the insert button and retract button may further be distinguishable according to tactile feel (e.g., by way of use of different button shapes, or different patterns of raised dots or other textured identification differing between the inset and retract buttons). In some examples, the insert button and retract button may be arranged opposite of one other on the face of the horizontal rotary control 302, while in other examples, the insert button and retract button may be arranged to be relatively adjacent to one another.

Figure 3D:
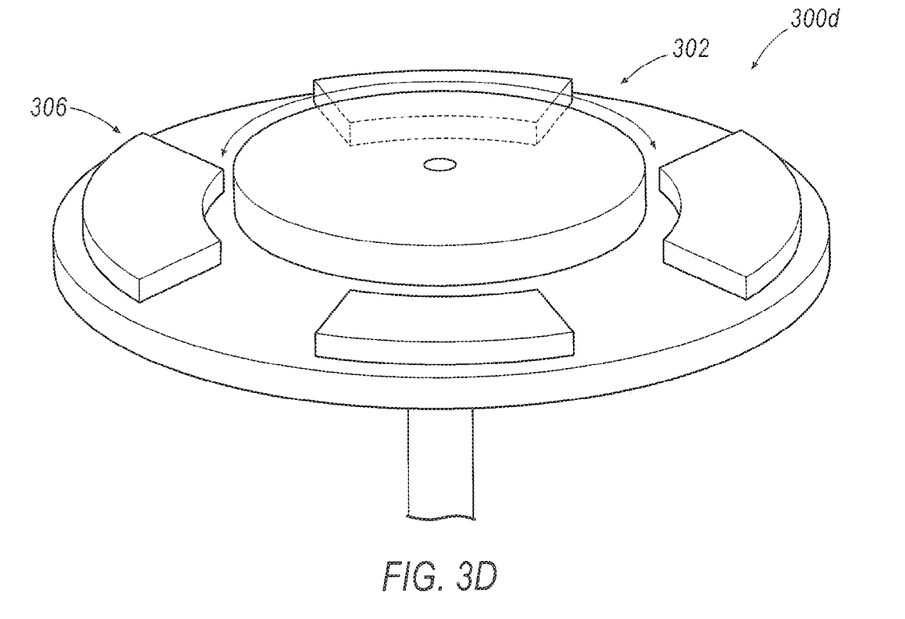
FIG. 3D illustrates an alternate exemplary device including a horizontal rotary control and a directional pad for catheter control.

FIG. 3D illustrates an alternate exemplary device 300-D including a horizontal rotary control 302 and directional pad guide wire control sensors 306. As with the device 300-A through 300-C, the device 300-D may provide for rotational control of the guide wire 108 according to a horizontal rotary control 302. However, to provide for guide wire 108 insertion control, rather than using buttons that rotate with the horizontal rotary control 302 as described with respect to the device 300-C, the device 300-D may include directional pad guide wire control sensors 306 mounted about the horizontal rotary control 302. In some cases the directional pad guide wire control sensors 306 may be mounted to the support for the horizontal rotary control 302, while in other cases the horizontal rotary control 302 may be mounted to the directional pad guide wire control sensors 306 instead. The (typically) four buttons of the directional pad guide wire control sensors 306 may be mapped to various guide wire 108 control functions. As one example, an "up" directional pad guide wire control sensor 306 may be mapped to insert, a "down" sensor 306 to retract, and "left" and "right" sensors 306 to opposite directions of articulation of the guide wire 108.

Figure 4A:
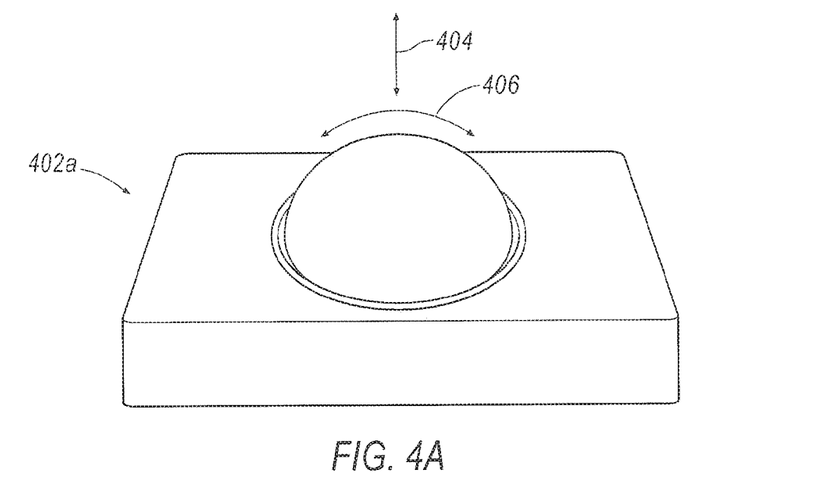
FIG. 4A illustrates an exemplary device including a trackball control.

FIG. 4A illustrates an exemplary trackball control 402-A. A trackball control 402 may be any of various devices including a ball element held by a socket, the socket containing sensors to detect a rotation of the ball about two axes. An exemplary trackball control 402 may be of a small size, such as one centimeter in diameter, to provide for easy control of both axes. However, trackballs of larger or smaller diameters may be utilized as well. To measure the rotation of the trackball, the trackball control 402 may include wheels in contact with the trackball in orthogonal directions (i.e., for X and Y axes of rotation). Optical or Hall Effect sensors may be coupled to the contact wheels to derive positioning information from the movement of the wheels against the trackball. Motion of the trackball control 402 about the Y-axis 404 may be mapped to the guide wire 108 insert and retract function, while motion in the X direction 406 may be mapped to guide wire 108 roll.

Because trackball control 402 motion may be infinite in both X and Y axes, the trackball control 402 may be suitable for relative position control in insert and retract. In some examples, to facilitate operator input of fast motions, the insert direction may include an inertia control such that once a certain degree of rotation in the insert Y-axis direction in achieved, the trackball control 402 may transition to the velocity control mode as discussed above. Thus, once in the velocity control mode, the guide wire 108 may continue to insert until the operator moves the trackball again (e.g., in a direction corresponding to retract), thereby reducing the velocity or exiting velocity control mode and returning the exemplary trackball control 402 to a non-velocity control mode of control.

Figure 4B:
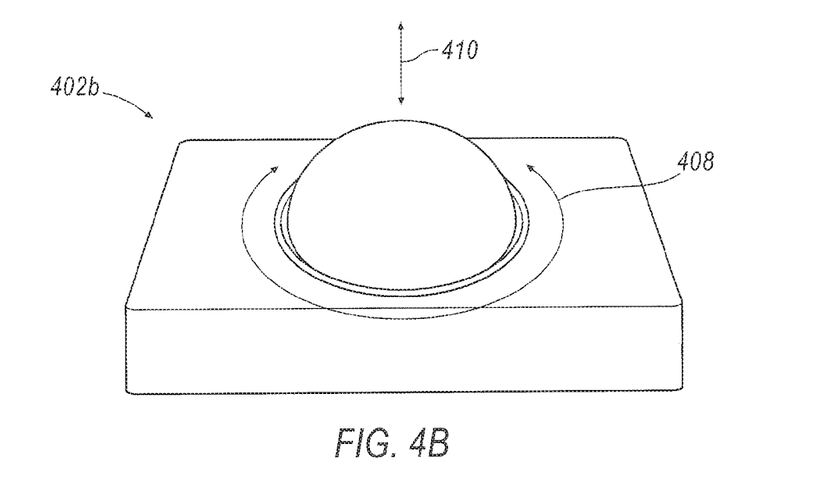
FIG. 4B illustrates an alternate exemplary device including a trackball control.

As another possibility, as shown in FIG. 4B, another control scheme using the trackball control 402 may include use of the circular direction of the trackball 408 as roll and radial movement of the trackball 410 as performing insertion and retraction motions. As yet a further possibility the track ball concept could be applied to a touchpad, where swipe gestures in an X-axis may provide roll positioning and swipe gesture in a Y-axis may provide for positioning.

Thus, a device, such as the devices 200-400 discussed in detail above, may be mounted to a control member of a joystick 122 and may be designed to allow for simultaneous guide wire 108 roll and guide wire 108 insertion controlled by a single digit of an operator hand, allowing the rest of the operator hand to control a catheter 106. By providing rotational control of the guide wire 108 according to a rotary control device and also axial control of the guide wire 108 (e.g., insert, retract) according to an insertion control, the device may provide for single-digit control of features such as simultaneous roll and insertion of a guide wire 108, without requiring the operator to work with a second set of guide wire 108 or other controls in another hand.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein. The software executed by the operator workstation 114 may be one such computer program product. In some example, the operator workstation 114 software when executed by one or more processors may provide the operations described herein. Alternatively, the software may be provided as hardware or firmware, or combinations of software, hardware and/or firmware.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A robotic system for manipulating an elongate body, the system comprising:
    an instrument driver operatively coupled to the elongate body; and
    an operator workstation communicatively coupled to the instrument driver, wherein the operator workstation comprises a control device comprising:
        a rotary member configured to receive a user input from an operator for controlling the elongate body,
        wherein the rotary member is movable in two dimensions, wherein motion in a first dimension of the two dimensions causes the instrument driver to direct movement of the elongate body in a first degree of freedom and motion in a second dimension of the two dimensions causes the instrument driver to direct movement of the elongate body in a second degree of freedom,
        wherein the control device comprises a velocity control mode in which the elongate body is configured to continuously move at a set velocity in the second degree of freedom based on a first signal from the rotary member indicative of user manipulation in a first direction of the second dimension, and
        wherein the control device further comprises a position control mode in which the elongate body is configured to move at an adjustable velocity in the second degree of freedom controlled by a second signal from the rotary member indicative of user manipulation in a second direction of the second dimension.

2. The robotic system of claim 1, wherein the rotary member comprises a ball element held by a socket.

3. The robotic system of claim 2, wherein the ball element is infinitely rotatable within the socket in at least the two dimensions.

4. The robotic system of claim 2, wherein the socket contains a plurality of sensors for detecting rotation of the ball element about the two dimensions.

5. The robotic system of claim 4, further comprising a plurality of contact wheels coupled to the plurality of sensors, wherein the contact wheels are in contact with the ball element.

6. The robotic system of claim 4, wherein each of the plurality of sensors comprises at least one of optical sensors or Hall effect sensors.

7. The robotic system of claim 1, wherein the rotary member is a trackball.

8. The robotic system of claim 1, wherein the two dimensions comprise an X axis and a Y axis.

9. The robotic system of claim 1, wherein motion along the first dimension causes the instrument driver to rotate the elongate body about a longitudinal axis of the elongate body.

10. The robotic system of claim 1, wherein motion along the second dimension causes the instrument driver to at least one of advance or retract the elongate body along a longitudinal axis.

11. The robotic system of claim 1, wherein movement in the second degree of freedom comprises at least one of axial insertion or retraction of the elongate body.

12. The robotic system of claim 11, wherein motion of the rotary member in the second dimension beyond a preset degree of rotation causes the control device to transition from the relative position control mode to the velocity control mode.

13. The robotic system of claim 1, wherein the adjustable velocity of the elongate body is capped at a predefined velocity limit.

14. The robotic system of claim 10, wherein the control device comprises a relative or actual position control mode for controlling movement of the elongate body in the first degree of freedom, wherein movement in the first degree of freedom comprises rotation of the elongate body about the longitudinal axis.

15. The robotic system of claim 1, wherein the elongate body comprises a guidewire.

16. A method for manipulating an elongate body, the method comprising:
    providing a robotic system, the system comprising:
        an instrument driver operatively coupled to the elongate body; and
        an operator workstation communicatively coupled to the instrument driver, wherein the operator workstation comprises a control device comprising a rotary member movable in two dimensions;
    moving the rotary member of the control device in a first dimension of the two dimensions,
    wherein motion in the first dimension of the two dimensions causes the instrument driver to direct movement of the elongate body in a first degree of freedom and motion in a second dimension of the two dimensions causes the instrument driver to direct movement of the elongate body in a second degree of freedom,
    moving the rotary member of the control device in a velocity control mode to continuously move the elongate body at a set velocity in the second degree of freedom based on a first signal from the rotary member indicative of user manipulation in a first direction of the second dimension, and moving the rotary member of the control device in a position control mode to move the elongate body at an adjustable velocity in the second degree of freedom controlled by a second signal from the rotary member indicative of user manipulation in a second direction of the second dimension.

17. The method of claim 16, wherein the rotary member comprises a ball element held by a socket.

18. The method of claim 17, wherein the ball element is infinitely rotatable within the socket in at least the two dimensions.

19. The method of claim 17, wherein the socket contains a plurality of sensors for detecting rotation of the ball element about the two dimensions.

20. The method of claim 19, wherein the system further comprises a plurality of contact wheels coupled to the plurality of sensors, and the contact wheels are in contact with the ball element.

21. The method of claim 19, wherein each of the plurality of sensors comprises at least one of optical sensors or Hall effect sensors.

22. The method of claim 16, wherein the rotary member is a trackball.

23. The method of claim 16, wherein the two dimensions comprise an X axis and a Y axis.

24. The method of claim 16, wherein motion along the first dimension causes the instrument driver to rotate the elongate body about a longitudinal axis of the elongate body.

25. The method of claim 16, wherein motion along the second dimension causes the instrument driver to at least one of advance or retract the elongate body along a longitudinal axis.

26. The method of claim 25, wherein the control device comprises a relative or actual position control mode for controlling movement of the elongate body in the first degree of freedom, wherein movement in the first degree of freedom comprises rotation of the elongate body about the longitudinal axis.

27. The method of claim 25, wherein movement in the second degree of freedom comprises at least one of axial insertion or retraction of the elongate body.

28. The method of claim 27, wherein the motion of the rotary member in the second dimension beyond a preset degree of rotation causes the control device to transition from the position control mode to the velocity control mode.

29. The method of claim 16, wherein the elongate body comprises a guidewire.

30. A robotic system for manipulating an elongate body, the system comprising:
an instrument driver operatively coupled to the elongate body; and
an operator workstation communicatively coupled to the instrument driver, wherein the operator workstation comprises a control device comprising:
a rotary member configured to receive a user input from an operator for controlling the elongate body,
wherein the rotary member is movable in two dimensions,
wherein motion in a first dimension of the two dimensions causes the instrument driver to direct movement of the elongate body in a first degree of freedom and motion in a second dimension of the two dimensions causes the instrument driver to direct movement of the elongate body in a second degree of freedom,
wherein motion along the second dimension causes the instrument driver to at least one of advance or retract the elongate body along a longitudinal axis,
wherein the control device comprises a relative position control mode and a velocity control mode for controlling movement of the elongate body in the second degree of freedom,
wherein movement in the second degree of freedom comprises at least one of axial insertion and retraction of the elongate body, and
wherein motion of the rotary member in the second dimension beyond a preset degree of rotation causes the control device to transition from the relative position control mode to the velocity control mode.

* * * * *